(12) United States Patent
Juhasz et al.

(10) Patent No.: US 6,648,877 B1
(45) Date of Patent: *Nov. 18, 2003

(54) METHOD FOR CUSTOM CORNEAL CORRECTIONS

(75) Inventors: Tibor Juhasz, Irvine, CA (US); Ronald M. Kurtz, Ann Arbor, MI (US); Christopher Horvath, Irvine, CA (US); Carlos G. Suarez, Irvine, CA (US); J. Randy Alexander, Newport Beach, CA (US)

(73) Assignee: Intralase Corp., Irvine, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 56 days.

(21) Appl. No.: 09/609,090

(22) Filed: Jun. 30, 2000

(51) Int. Cl.$^7$ ................................................ A61P 9/007
(52) U.S. Cl. ................................. 606/5; 606/10; 606/12; 606/13
(58) Field of Search ............................. 606/3, 5, 10–13

(56) References Cited

U.S. PATENT DOCUMENTS

| | | | | |
|---|---|---|---|---|
| 4,903,695 A | * | 2/1990 | Warner et al. | 606/4 |
| 4,907,586 A | * | 3/1990 | Bille et al. | 606/5 |
| 6,099,522 A | * | 8/2000 | Knopp et al. | 606/3 |

* cited by examiner

Primary Examiner—David M. Shay
(74) Attorney, Agent, or Firm—Fulbright & Jaworski L.L.P.

(57) ABSTRACT

A method for customizing corneal corrections includes superposing an imaginary reference field (grid) on the anterior surface of the cornea of an eye to divide the corneal surface into reference areas. Also, a diagnostically determined refractive power map for the cornea is created. An incising laser beam is then directed through an individual reference area to a focal spot. Next, movement of the focal spot along the laser beam path is selectively accomplished to photoalter a predetermined volume of stromal tissue. Subsequently, based on the refractive power map, the predetermined volume of stromal tissue that is to be photoaltered is identified for each specific reference area. Accordingly, the steps of directing the beam and moving the focal spot are then repeated using selected reference areas until the required corneal correction is achieved.

17 Claims, 1 Drawing Sheet

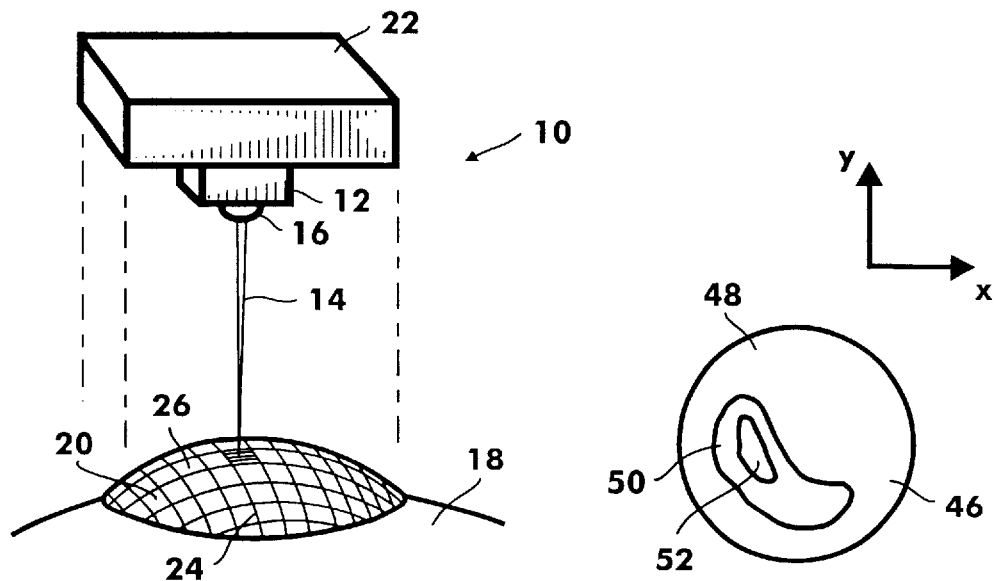
Fig. 1
Fig. 3
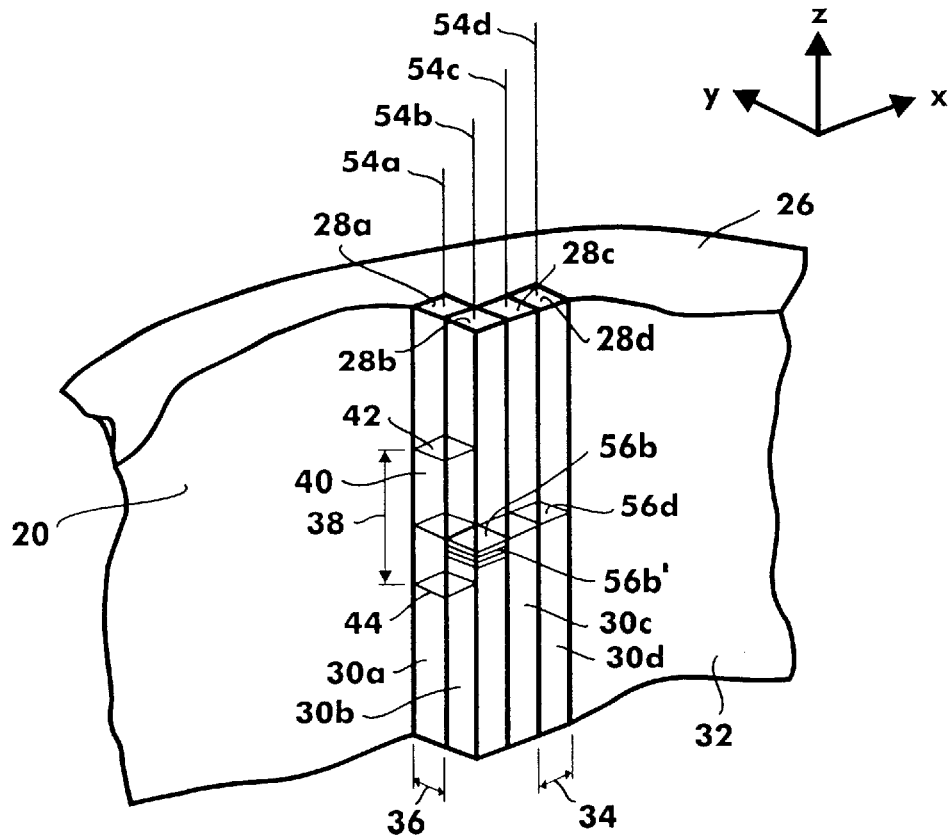
Fig. 2

METHOD FOR CUSTOM CORNEAL CORRECTIONS

FIELD OF THE INVENTION

The present invention pertains generally to ophthalmic surgical procedures which use pulsed laser beams to photoalter tissue of the cornea. More particularly, the present invention pertains to ophthalmic surgical procedures which effect the correction of optical aberrations identified by reference to diagnostically predetermined refractive power maps. The present invention is particularly, but not exclusively, useful for conducting an ophthalmic surgical procedure that is customized to correct the specific optical aberrations of a particular eye.

BACKGROUND OF THE INVENTION

Optical aberrations of an eye generally manifest themselves as asymmetric distortions relative to the optical axis of the eye. Further, they are typically non-spherical in their geometry. Consequently, in order to successfully accomplish high-accuracy corrections of these optical aberrations, it is necessary to have detailed and accurate information about the optical aberrations. It is also necessary to have a surgical instrument that is capable of precisely and accurately performing the necessary surgical procedures.

Non-ultraviolet, ultrashort pulsed laser technology has now advanced to the point where pulsed laser beams can be produced that have pulses with durations measured in femtoseconds. For example, see U.S. Pat. No. 5,993,438 which issued to Juhasz et al. for an invention entitled "Intrastromal Photorefractive Keratectomy" (hereinafter the Juhasz Patent). Importantly, it is known that a device as disclosed in the Juhasz Patent is effective for performing ophthalmic surgical procedures with the precision that is required for high-accuracy corrections of optical aberrations.

As indicated above, in addition to having an effective surgical laser, it is also important to have detailed information about the optical aberrations that are to be corrected. Specifically, it is necessary to know the extent of the desired correction, and the location in the cornea of the eye where the correction can be made most effectively. For these purposes, it is necessary to precisely determine the refractive power of the cornea. It happens that wavefront analysis techniques, made possible by devices such as the well-known Hartmann-Shack type sensor, can be used to generate maps of corneal refractive power. These maps, or similar refractive power information provided by other means such as corneal topographs, can then be used by the ophthalmic surgeon to identify and locate the optical aberrations of a cornea that require correction.

In light of the above, it is an object of the present invention to provide a device, and a method for using the device, that can customize corneal corrections by effectively using a refractive power map as a tool for guiding an incising laser beam. It is another object of the present invention to provide a device, and a method for using the device, that effectively confines the photoalteration of corneal tissue to only the volume of tissue that is required to achieve the desired optical corrections for the cornea. Still another object of the present invention is to provide a device, and a method for using the device, that is easy to implement, simple to use, and comparatively cost effective.

SUMMARY OF THE PREFERRED EMBODIMENTS

In accordance with the present invention, a method for customizing corneal corrections includes first obtaining information about the optical aberrations of the particular eye that is to be corrected. Typically, this information will be in the form of a refractive power map, such as a corneal topograph. As is well known, refractive power maps of this type can be generated using wavefront analysis techniques that will show the amount of correction required in each particular area of the cornea.

With the refractive power map in mind, an imaginary reference field (grid) is superposed on the anterior surface of the cornea of the eye. The purpose of this imaginary reference field (grid) is really two-fold. First, the imaginary reference field (grid) is used to divide the corneal surface into a plurality of individual reference areas that can be identified with corresponding portions of the refractive power map. Second, the reference areas provide targets for control in aiming, or directing, an incising laser beam toward the stromal tissue that is to be photoaltered. Further, by projecting each of the reference areas from the anterior surface through the cornea, the reference areas can be extended to define respective reference volumes. As contemplated by the present invention, the reference area will be generally square and quite small, with sides on the order of about ten microns in length. The reference volume will then extend through the cornea between the anterior and posterior surfaces of the cornea.

In operation, the incising laser beam is directed along a beam path and through a selected reference area to a focal spot. The stromal tissue at the focal spot is then photoaltered. It is known that lasers may be used for plasma mediated tissue ablation (generally superficial tissue) and for plasma mediated tissue disruption (generally internal bulk tissue). With this in mind, the term photoalteration is used in the context of the present invention to indicate an operation wherein there may be either plasma mediated tissue ablation or plasma mediated tissue disruption. Preferably, for the present invention, the incising laser beam is a non-ultraviolet ultrashort-pulsed laser beam having a plurality of pulses that each have a duration greater than approximately ten femtoseconds.

While the incising laser beam is activated, its focal spot is selectively moved along the beam path to photoalter stromal tissue through a predetermined length of the beam path. The incising laser beam is then redirected through another reference area and the process of photoalteration is repeated. In particular, the sequence for directing the incising laser beam through individually selected reference areas, and the extent of stromal tissue photoalteration while the incising laser beam is so directed, can be varied as required. Specifically, as indicated above, the amount of photoalteration will be determined by the refractive power map. On the other hand, the sequence of reference areas that is followed during a customized procedure will depend on the particular objectives of the procedure.

As a complementary procedure, the present invention envisions a LASIK type procedure wherein a flap is cut into the cornea to establish extracorporeal access to the tissue that is to be photoaltered. Once access has been achieved, the photoalteration is accomplished and the residual fragments of the photoaltered tissue are mechanically removed from the cornea. In another complementary procedure, it is envisioned that the photoalteration of intrastromal tissue will result in the creation of an isolated lenticle of intrastromal tissue. For this procedure, once the lenticle of tissue has been created it can be mechanically removed from the cornea.

In all of the customized procedures contemplated by the present invention, photoalteration of stromal tissue will be accomplished in accordance with the dictates of a refractive power map. Thus, regardless whether the procedure creates a lenticle or generates residual fragments that require subsequent removal from the cornea, or whether photoalteration alone is sufficient, the result is a customized reconfiguration of the cornea that will correct the specific optical aberrations of a particular eye.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 1 is a perspective view of a cornea of an eye with an imaginary reference field (grid) superposed thereon;

FIG. 2 is a perspective view of a portion of the cornea of an eye showing the geometrical relationships between the corneal anatomy and the focal spot of an incising laser beam; and FIG. 3 is a plan view of a refractive power map of a cornea.

DESCRIPTION OF THE PREFERRED EMBODIMENT

Referring initially to FIG. 1, an ophthalmic laser system for accomplishing the methods of the present invention is shown and is generally designated 10. As shown, the device 10 includes a laser source 12 which is capable of generating a non-ultraviolet, ultrashort-pulsed incising laser beam 14. Focusing optics 16, which have components that are well-known in the pertinent art, are provided for directing and focusing the incising laser beam 14. As intended for the present invention, the focusing optics 16 will direct the incising laser beam 14 toward the eye 18. More specifically, the focusing optics 16 will focus the incising laser beam 14 either onto the cornea 20 for plasma mediated (non-UV) photoablation of superficial tissue, or into the stroma of the cornea 20 for intrastromal photodisruption of tissue (i.e. photoalteration).

FIG. 1 also shows that the device 10 includes a reference unit 22 that will be used to establish a reference field (i.e. imaginary grid) 24 on the anterior surface 26 of the cornea 20. Specifically, as envisioned for the present invention, the imaginary reference field (grid) 24 is electronically generated by the reference unit 22 to identify a plurality of reference areas 28 on the anterior surface 26. These reference areas 28 can then be used for purposes of controlling the direction of the incising laser beam 14 toward the cornea 20. As shown in FIG. 2, the specific reference areas 28a, 28b, 28c and 28d are only exemplary. Further, the grid lines that are illustrated in FIG. 1 to establish the various reference areas 28 are presented only for purposes of disclosing the relationship of the reference areas 28 to each other, and to the cornea 20. Stated differently, in practice, the reference areas 28 will be electrically identified in the reference unit 22, and will not necessarily be visible on the anterior surface 26 of the cornea 20.

With reference now to FIG. 2, it will be appreciated that the respective reference areas 28a–d can be used to establish reference volumes 30a–d that extend through the stroma of the cornea 20. More specifically, each reference volume 30 extends through the cornea 20 from the anterior surface 26 to the posterior surface 32. The actual size of each reference volume 30 will thus depend on the thickness of the cornea 20 and the lengths of the x-dimension 34 and y-dimension 36 of the respective reference area 28. As envisioned for the present invention, the x-dimension 34 and the y-dimension 36 will preferably be around ten microns in length.

FIG. 2 also shows that within a particular reference volume 30 a length 38 can be established which will define a tissue volume 40. For example, the tissue volume 40 shown in FIG. 2 is located within a projection of the reference area 28a through the cornea 20, and is bounded between the end 42 and the end 44. As will be appreciated by the skilled artisan, the size of a tissue volume 40 will depend on the size of the respective reference area 28 and the extent of length 38. For the purposes of the present invention, the extent of length 38 is diagnostically determined.

FIG. 3 is a plan view of a representative refractive power map 46 that has been diagnostically determined for a cornea 20. As indicated above, a refractive power map 46 can be generated using optical techniques that are well known in the pertinent art, such as by wavefront analysis. Once generated, the refractive power map 46 effectively indicates those portions of the cornea 20 that contribute to the optical aberrations. For example, if the area 48 of the refractive power map 46 is considered equivalent to a normal eye 18, the area 50 will indicate a deviation from this norm that requires some optical correction. Specifically, the correction required for the deviation will be stated in diopters. Further, the area 52 will indicate a deviation from the norm where additional optical correction is required. With the areas 48, 50 and 52 properly identified, it is well known that the removal or alteration of precise amounts of stromal tissue from selected areas of the cornea 20 (e.g. areas 50 and 52), will result in the desired optical correction.

In the operation of the device 10 of the present invention, the refractive power map 46 for the cornea 20 is created first. The map 46 is then analyzed to identify areas on the map 46 that correspond with the imaginary reference field (grid) 24 that is generated in the reference unit 22. Thus, the map 46 is correlated with reference areas 28 of the reference field (grid) 24 and the contribution each reference volume 30 makes to the optical aberrations of cornea 20 is determined. Based on this information, the size of the tissue volume 40 that is to be removed from the reference volume 30 is determined.

In order to remove tissue from the cornea 20, the laser source 12 is activated, and the focusing optics 16 are also activated to direct an incising laser beam 14 along a beam path 54. As shown, with this control, the incising laser beam 14 can be directed toward a preselected reference area 28 on the anterior surface 26 of the cornea 20 (the beam paths 54a, 54b, 54c and 54d are only exemplary). By way of example, the incising laser beam 14 can be directed along the beam path 54b for incidence on the reference area 28b. The incising laser beam 14, when so directed, can then be focused onto the reference area 28b, or be passed through the reference area 28b and focused to a focal spot 56b in the reference volume 30b. In either case, the incising laser beam 14 is focused in a manner which will cause it to photoalter the tissue at the focal spot 56.

As intended for the present invention, the incising laser beam 14 can be selectively redirected to move from one focal spot 56 to another focal spot 56. Also, the incising laser beam 14 can be moved from a focal spot 56 in one reference volume 30 to a focal spot 56 in another reference volume 30. For example, the incising laser beam 14 can be focused to the focal spot 56*b* in reference volume 30*b* and, subsequently, focused to the focal spot 56*b'* in the reference volume 30*b*. Similarly, the incising laser beam 14 can be subsequently focused to the focal spot 56*d* in reference volume 30*d*. Thus, the focal spot 56 of the incising laser beam 14 can be moved, as desired, in the x-direction and in the y-direction. Additionally, the focal spot can be moved along the length 38 in a predetermined tissue volume 40 (Z direction). In this manner, predetermined volumes of stromal tissue, such as a lenticle, can be isolated in the stroma for subsequent removal. Also, layers of stromal tissue can be photoaltered to create passageways through the stroma. Further, whole volumes of tissue can be photoaltered, and the resultant debris removed. In each case, the removal of stromal tissue can be customized. Stated differently, the objective is to remove the stromal tissue, and only the stromal tissue, that will make whatever optical corrections are necessary.

While the particular Method for Custom Corneal Corrections as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A system for customizing asymmetrical or non-spherical corneal corrections which comprises:

a means for creating a refractive power map for the cornea;

a means for establishing a reference field relative to the outer surface of the cornea to divide the corneal surface into a plurality of reference areas;

a means for corresponding said refractive power map with said reference field to determine a refractive power correction for each said reference area;

a means for extending the reference field into the cornea to create a plurality of three-dimensional reference volumes inside the cornea;

a means for determining the amount of tissue to be removed from each reference volume to obtain the required refractive change;

a means for directing an incising laser beam along a beam path through at least one of said reference areas to a focal spot at a predetermined depth along the corresponding reference volume, to photoalter stromal along a predetermined length of said beam path;

a means for selectively moving said focal spot along said beam path to photoalter stromal tissue along a predetermined length of said beam path;

a means for activating said incising laser beam while the beam is being selectively moved to effectuate said refractive power correction for said reference area; and a means for redirecting said incising beam through another said reference area to photoalter stromal tissue.

2. A method for surgically correcting asymmetrical or non-spherical optical aberrations of an eye which comprises the steps of:

establishing a plurality of reference volumes in the cornea of the eye;

identifying a contribution from each said reference volume at a given depth below the surface of the cornea associated with the optical aberrations;

determining a tissue volume in each said reference volume;

directing an incising laser beam along a beam path into at least one of said reference volumes at a predetermined depth to photoalter said tissue volume therein and eliminate the contribution from said reference volume to the optical aberrations; and redirecting said incising laser beam into other said reference volumes to respectively photoalter said tissue volume at a predetermined depth therein and eliminate the contribution from each said reference volume to the asymmetrical or non-spherical optical aberrations.

3. A method as recited in claim 2 wherein said directing step and said redirecting step further comprise the steps of:

focussing said incising laser beam to a focal spot in said reference volume; and selectively moving said focal spot along said beam path to photoalter stromal tissue along a predetermined length of said beam path.

4. A method as recited in claim 2 further comprising the steps of:

cutting into the cornea to establish extracorporeal access with the photoaltered tissue; and removing fragments of the photoaltered tissue from the cornea.

5. A method as recited in claim 2 further comprising the steps of:

repeating said redirecting step to isolate a volume of intrastromal tissue; and removing the volume of intrastromal tissue from the cornea.

6. A method as recited in claim 2 wherein said incising laser beam is created using a non-ultraviolet ultrashort-pulsed laser and wherein said incising laser beam comprises a plurality of pulses with each said pulse having a duration greater than approximately ten femtoseconds.

7. A method as recited in claim 2 wherein said establishing step further comprises the steps of:

establishing a reference field for the cornea to divide the corneal surface into a plurality of reference areas; and projecting each said reference area from the anterior surface through the cornea to define respective said reference volumes.

8. A method as recited in claim 7 wherein said identifying step further comprises the steps of:

creating a refractive power map for the cornea; and corresponding said refractive power map with said reference field to determine the contribution from each said reference volume associated with the optical aberrations.

9. A method for customizing corrections of asymmetrical or non-spherical distortions in the cornea of an eye, which comprises the steps of:

creating a refractive power map for the cornea;

establishing a reference field relative to the outer surface of the cornea to divide the corneal surface into a plurality of reference areas;

corresponding said refractive power map with said reference field to determine a refractive power correction for each said reference area;

extending the reference field into the cornea to create a plurality of three-dimensional reference volumes inside the cornea;

determining the amount of tissue to be removed from each reference volume to obtain the required refractive change;

directing an incising laser beam along a beam path through at least one of said reference areas to a focal spot at a predetermined depth along the corresponding reference volume, to photoalter stromal tissue at said focal spot;

activating the laser to photoalter stromal tissue at a predetermined depth within the reference volume to effectuate said refractive power correction for the corresponding reference area to photoalter stromal tissue along a predetermined length of said beam path such that said incising laser beam is activated during said selectively moving step to effectuate said refractive power correction for said reference area; and redirecting said incising beam through another said reference area to photoalter stromal tissue in said another reference area.

10. A method as recited in claim 9 wherein said refractive power map includes a corneal topograph.

11. A method as recited in claim 9 wherein said refractive power map is produced using a wavefront analysis.

12. A method as recited in claim 1 further comprising the steps of:

cutting into the cornea to establish extracorporeal access with the photoaltered tissue; and removing fragments of the photoaltered tissue from the cornea.

13. A method as recited in claim 9 further comprising the steps of:

repeating said redirecting step to isolate a volume of intrastromal tissue; and removing the volume of intrastromal tissue from the cornea.

14. A method as recited in claim 9 wherein each said reference area has an x-dimension and a y-dimension.

15. A method as recited in claim 14 wherein said x-dimension is substantially equal to said y-dimension, and further wherein said x-dimension and said y-dimension are equal to approximately five microns.

16. A method as recited in claim 9 wherein said incising laser beam is created using a non-ultraviolet ultrashort-pulsed laser.

17. A method as recited in claim 16 wherein said incising laser beam comprises a plurality of pulses with each said pulse having a duration greater than approximately ten femtoseconds.

* * * * *